(12) United States Patent
Maschke

(10) Patent No.: US 8,611,495 B2
(45) Date of Patent: Dec. 17, 2013

(54) BIPLANE X-RAY IMAGING SYSTEM

(75) Inventor: Michael Maschke, Lonnerstadt (DE)

(73) Assignee: Siemens Aktiengesellschaft, München (DE)

( * ) Notice: Subject to any disclaimer, the term of this patent is extended or adjusted under 35 U.S.C. 154(b) by 220 days.

(21) Appl. No.: 13/103,246

(22) Filed: May 9, 2011

(65) Prior Publication Data
US 2011/0274246 A1 Nov. 10, 2011

(30) Foreign Application Priority Data

May 10, 2010 (DE) .......................... 10 2010 019 990

(51) Int. Cl.
G01N 23/04 (2006.01)

(52) U.S. Cl.
USPC ............................................ 378/62; 378/197

(58) Field of Classification Search
USPC ................................ 378/62, 197, 9, 36, 82, 92
See application file for complete search history.

(56) References Cited

U.S. PATENT DOCUMENTS

| 7,020,235 | B2 | 3/2006 | Hornegger et al. | |
| 7,359,484 | B2 | 4/2008 | Qiu et al. | |
| 2003/0142790 | A1* | 7/2003 | Zhou et al. | 378/119 |
| 2004/0066906 | A1* | 4/2004 | Hornegger et al. | 378/197 |
| 2006/0120507 | A1 | 6/2006 | Brunner et al. | |
| 2007/0183560 | A1 | 8/2007 | Popescu et al. | |
| 2007/0183563 | A1* | 8/2007 | Baumann et al. | 378/19 |
| 2007/0189449 | A1* | 8/2007 | Baumann et al. | 378/44 |
| 2008/0247506 | A1* | 10/2008 | Maschke | 378/15 |
| 2009/0074139 | A1* | 3/2009 | Hempel et al. | 378/62 |
| 2009/0154640 | A1* | 6/2009 | Baumann et al. | 378/19 |

FOREIGN PATENT DOCUMENTS

| DE | 10 2006 037 256 A1 | 8/2007 |
| DE | 10 2007 036 559 A1 | 2/2009 |
| DE | 10 2008 019 646 A1 | 10/2009 |
| EP | 1 879 020 A1 | 1/2008 |
| EP | 2 138 098 A1 | 12/2009 |
| EP | 1 803 398 B1 | 7/2010 |

OTHER PUBLICATIONS

Siemens AG, Healthcare Sector, Artis zee, "Advanced applications in interventional radiology", www.siemens.com/healthcare, Order No. A91AX-20822-12C1-766, Printed in Germany, © Jan. 2009 Siemens AG; pp. 1-14, Others; 2009.

* cited by examiner

Primary Examiner — Glen Kao

(57) ABSTRACT

A biplane X-ray imaging system is provided. The biplane X-ray imaging system has two recording units disposed in different planes. Each of the recording units has an X-ray detector and an X-ray source. The first recording unit is a phase-contrast recording unit for phase-contrast X-ray imaging. The second recording unit is a conventional recording unit for conventional x-ray imaging.

11 Claims, 3 Drawing Sheets

BIPLANE X-RAY IMAGING SYSTEM

CROSS REFERENCE TO RELATED APPLICATIONS

This application claims priority of German application No. 10 2010 019 990.7 filed May 10, 2010, which is incorporated by reference herein in its entirety.

FIELD OF THE INVENTION

The invention relates to a biplane X-ray imaging system.

BACKGROUND OF THE INVENTION

Minimally invasive interventions and minimally surgical interventional procedures on patients are increasingly replacing traditional surgical operations. A factor of crucial importance in this regard is good anatomical and functional medical imaging, in particular of soft tissue, in the case of interventions involving the heart and liver for example. For this reason known mobile C-arm X-ray machines using fluoroscopy imaging are not sufficient, since generally these only deliver 2D images with low soft-part resolution or their X-ray power is too low to achieve sufficiently good image quality for more complex interventions. Good 3D imaging is provided e.g. by a permanently mounted, ceiling-suspended C-arm X-ray system, such as the Artis Zee with DynaCT from the company Siemens AG for example. The functionality of the DynaCT is disclosed inter alia in US 2006/0120507 A1. At a pixel size of approx. 100 μm, a flat-panel detector based on solid-state material (e.g. amorphous silicon) possesses good spatial resolution, though in connection with conventional X-ray imaging this is not adequate for all applications, such as the visualization of tumor tissue for example.

U.S. Pat. No. 7,020,235 B2 discloses a conventional biplane X-ray system, the two recording planes of which in each case possess the same spatial resolution. Previously it was usually necessary to perform a biopsy of the tissue to be examined if the resolution of the X-ray images was no longer acceptable.

SUMMARY OF THE INVENTION

It is the object of the present invention to provide an X-ray imaging system which not only enables good image quality in respect of spatial resolution but also allows good visualization of soft tissue.

The object is achieved according to the invention by a biplane X-ray imaging system as claimed in the independent claim. Advantageous embodiments of the invention are in each case the subject matter of the associated dependent claims.

The biplane X-ray imaging system according to the invention has two recording units arranged in different planes, each such unit having an X-ray detector and an X-ray source, wherein the first recording unit is formed by a phase-contrast recording unit for phase-contrast X-ray imaging. Phase-contrast X-ray imaging exploits the fact that different types of body tissue diffract X-ray beams to different degrees. The phase shift effect when an X-ray beams passes through an examination subject is significantly stronger than the absorption effect of the material penetrated by the X-ray radiation. By means of phase-contrast X-ray imaging soft parts can be represented with particularly high contrast in X-ray examinations. In combination with a second, conventional recording unit (which measures the X-ray radiation attenuated through absorption in an examination subject) the biplane X-ray imaging system according to the invention can provide not only conventional projection images but also particularly high-quality visualizations of soft parts. This makes such a system also suitable for minimally invasive interventions and minimally surgical interventional procedures.

According to an embodiment of the invention the first recording unit embodied for phase-contrast X-ray imaging has an X-ray tube assembly, an X-ray detector, a phase grating which is disposed between an examination subject and the X-ray detector, and an amplitude grating which is disposed between the phase grating and the X-ray detector. In order to generate quasi-coherent X-ray radiation, as is required for phase-contrast X-ray imaging, two alternatives can be used: According to a first alternative the first recording unit has a further grating which is disposed behind the X-ray tube assembly of the first recording unit and is embodied for the purpose of generating coherent X-ray radiation from the non-coherent X-ray radiation of the X-ray tube assembly. According to a second alternative the X-ray tube assembly of the first recording unit has a plurality of field-emission X-ray sources for emitting quasi-coherent X-ray radiation. Integrating an X-ray tube assembly having field-emission X-ray sources into a phase-contrast X-ray imaging system eliminates the need for the complex source grating for generating monochromatic X-ray radiation, because the field-emission X-ray sources constitute a simple and effortless means of generating mutually coherent X-ray beams with a narrow focus. This enables the X-ray imaging system to be manufactured in a particularly compact design and particularly economically.

The fundamental idea behind phase-contrast X-ray imaging lies in finding the exact positions of interference lines generated by means of the phase grating from coherent X-ray radiation penetrating an examination subject and from these determining the phase shift caused by the examination subject. However, since the distances between the interference lines are in the micrometer range, a regular X-ray detector lacks sufficient resolution to image the interference lines or their maxima. For this reason an amplitude grating having low X-ray transparency and ideally the same periodicity and orientation as the interference lines is disposed directly in front of the X-ray detector and the interference lines are sampled by means of said grating.

The phase grating therefore generates an interference pattern which, with the aid of the amplitude grating, reproduces a moiré pattern on the X-ray detector disposed therebehind. If the amplitude grating is displaced slightly, this causes the moiré pattern to be shifted likewise, i.e. a change in the spatial intensity in the X-ray detector disposed therebehind which can be determined relative to the displacement of the amplitude grating. By plotting the change in intensity for each detector element of said grating, that is to say for each beam, as a function of the displacement path of the absorption grating it is possible to determine the phase shift of the respective beam. The amplitude grating thus fulfills the function of a transmission mask and converts local interference lines into intensity fluctuations. The measured signal profile contains quantitative information relating to the phase gradient of the examination subject.

The phase grating is structured two-dimensionally, for example, and possesses low X-ray absorption. At the same time it generates a significant phase shift, for example of $\pi$ or an uneven multiple thereof. The phase grating can be formed from silicon or a polymer for example. It can also be embodied as a beam splitter grating. The amplitude grating is likewise structured two-dimensionally and possesses high X-ray absorption. It is disposed for example in the radiation direction directly in front of the X-ray detector and fulfills the function of a noise suppression grating.

In the case of a field-emission X-ray source or, as the case may be, the corresponding field-emission cathode, electrons are emitted as a result of a sufficiently high electric field being applied. Field emission is achieved e.g. by means of a simple diode mode in which a bias voltage is applied between anode and cathode. Electrons are emitted by the cathode when the electric field exceeds the emission threshold. A triode construction can also be provided in which a gate electrode is disposed close to the cathode. Electrons are emitted here by applying a bias voltage between gate and cathode. The emitted electrons are then accelerated by means of a high voltage between gate and anode. Field-emission cathodes a very high, readily controllable and easily focusable electron beam current. All in all, by means of the field-emission X-ray sources the invention affords the advantages of low heat generation by the field-emission X-ray tube assembly and a low weight, not only on account of the field-emission tube assembly itself but also as a result of the omission or reduction in size of a cooling system. Furthermore such a field-emission tube assembly is highly compact in comparison with conventional X-ray tube assemblies, thereby establishing the precondition for providing a high-quality, laminar X-ray source having a surface area of many focal points arranged adjacent to one another. This is ensured in particular by means of an array having a plurality of field-emission tube assemblies. The useful life of field-emission tube assemblies is also significantly higher than that of known X-ray tube assemblies using thermal cathodes. In addition, by comparison with a thermal cathode a field-emission cathode can be started quickly without heating. Moreover, a higher spatial resolution can be achieved for X-ray images thanks to the readily focusable electron current.

According to an embodiment of the invention the field-emission X-ray source has in each case a field-emission cathode having a nanostructured material with carbon nanotubes (a so-called CNT (Carbon Nano Tube) cathode). Materials of this kind exhibit particularly good emission characteristics, are stable even at high currents, and furthermore can be manufactured in a particularly small format. Field-emission technology using CNT is known from U.S. Pat. No. 7,359,484 B2 for example.

The field-emission X-ray sources are beneficially arranged in an array, in other words, for example, in a two-dimensional, matrix-type arrangement, or alternatively in an arrangement consisting of one or more rows. By virtue of their small size the field-emission X-ray sources can be arranged very densely, thereby forming a surface area consisting of X-ray focal points. The individual field-emission X-ray sources can also be activated individually or in groups.

According to an embodiment of the invention the X-ray imaging system has means for moving the absorption grating or amplitude grating vertically with respect to the radiation direction. The means can be for example a motor or a piezoelectric actuator.

According to an embodiment of the invention the second recording unit has a flat-panel detector based on a solid-state material. The flat-panel detector can be formed for example on the basis of amorphous silicon (aSi) or cadmium telluride (CdTe) or cadmium zinc telluride (CZT) or CMOS, or it can have organic photodiodes. The flat-panel detector of the second recording unit is optimized in particular for a high spatial resolution during imaging.

According to another embodiment of the invention the first recording unit also has a solid-state-based flat-panel detector.

Both recording units beneficially have C-arms. The recording units are advantageously disposed on at least one robotic arm, in particular a 6-axis articulated-arm robot, in order to provide particularly good, quick and simple adjustability in three dimensions.

BRIEF DESCRIPTION OF THE DRAWINGS

The invention as well as further advantageous embodiments in accordance with features of the dependent claims are explained in more detail below with reference to exemplary embodiments, without this implying any limitation of the invention to said exemplary embodiments, as schematically depicted in the drawing, in which:

DETAILED DESCRIPTION OF THE INVENTION

Figure 1:
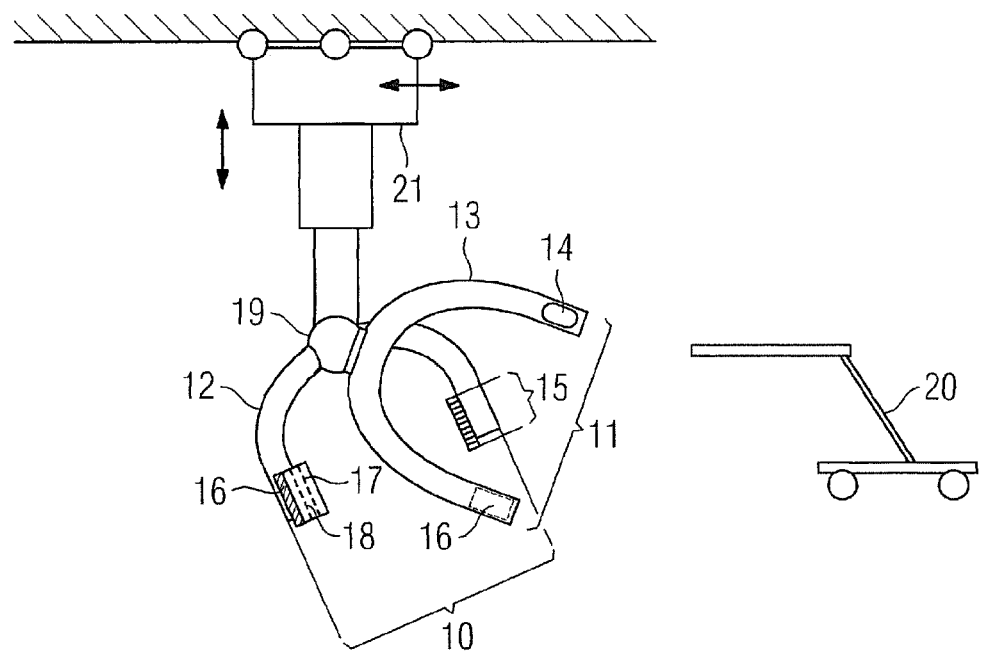
FIG. 1 shows a view of an inventive biplane X-ray imaging system for phase-contrast X-ray imaging with a ceiling stand.
Figure 2:
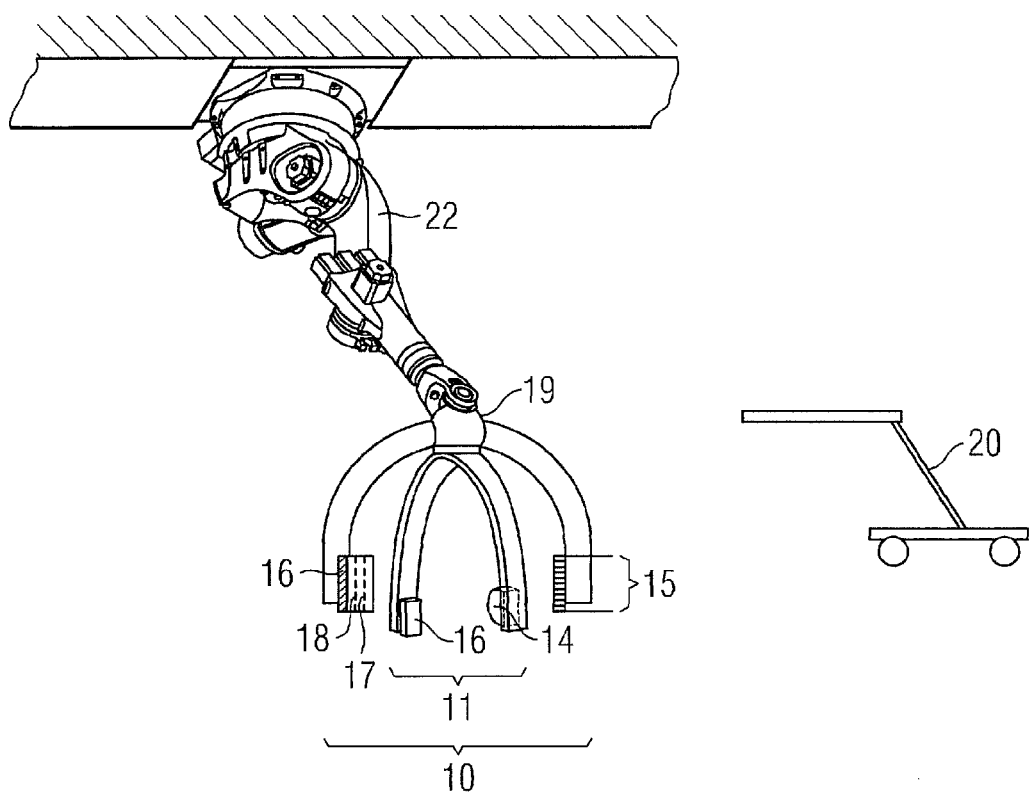
FIG. 2 shows a view of a further inventive biplane X-ray imaging system with articulated-arm robot.

FIG. 1 and FIG. 2 each show an inventive biplane X-ray imaging system having two recording units disposed in different planes, a first recording unit 10 embodied for phase-contrast X-ray imaging and a second, "conventional" recording unit 11 embodied for fluoroscopy imaging. The two recording planes are offset with respect to each other by e.g. 90°.

Figure 4:
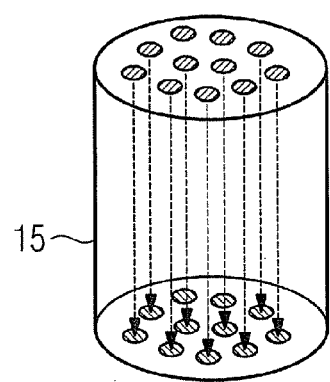
FIG. 4 shows a view of a field-emission tube assembly with a plurality of field-emission cathodes.
Figure 5:
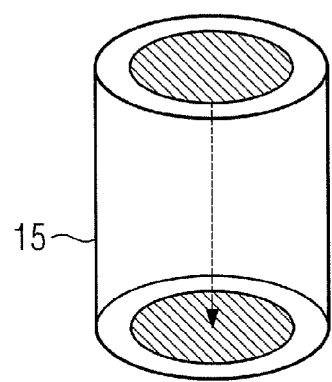
FIG. 5 shows a view of a field-emission tube assembly with one field-emission cathode.

The second, "conventional" recording unit 11 in the form of a second C-arm 13 has a conventional X-ray tube assembly 14 and an X-ray detector 16 which can be for example a solid-state-based flat-panel detector. Instead of the conventional X-ray tube assembly 14, a field-emission tube assembly 15 having a single field-emission cathode—as shown in FIG. 5—or a field-emission tube assembly 15 having a plurality of field-emission cathodes—as shown in FIG. 4—can also be used. It is also possible to use a plurality of field-emission tube assemblies 15, each having one field-emission cathode. In the case of the second recording unit 11, X-ray radiation is transmitted by the X-ray tube assembly through an examination subject, the X-ray radiation penetrates the examination subject and is partially reflected or, depending on the nature of the examination subject, absorbed and generates an X-ray (projection) image on the X-ray detector 16 disposed behind the examination subject. The generated X-ray image is based on the different absorption rate of X-ray beams in different materials, e.g. bone as opposed to soft tissue. The second recording unit 11 is particularly suitable for recording X-ray images of large regions, overview X-ray images for example. All in all, X-ray images having a high quality of temporal resolution.

In contrast, the first recording unit 10 embodied for phase-contrast X-ray imaging is particularly suitable for acquiring X-ray images of small regions with particularly high spatial resolution and high contrast ("X-ray magnifier") in order e.g.

to visualize tumor tissue in detail. The first recording unit 10, likewise in the form of a first C-arm 12, has a field-emission tube assembly 15, a phase grating 17, an amplitude grating 18 and an X-ray detector 16. The field-emission tube assembly 15 has e.g. a plurality of field-emission cathodes (see FIG. 4) which are arranged for example in an array which has a matrix-like structure. The field-emission cathodes can also be arranged in a row or column layout. A plurality of uniformly arranged, ideally homogeneous field-emission X-ray sources can, upon being activated, generate coherent X-ray radiation in a simple manner and without the use of a coherence grating. Optionally it is also possible to activate individual field-emission X-ray sources or some of the field-emission X-ray sources. As an alternative to the field-emission tube assembly 15, a conventional X-ray tube assembly having a coherence grating disposed therebehind can also be provided for the purpose of converting the X-ray radiation into coherent X-ray radiation.

Figure 3:
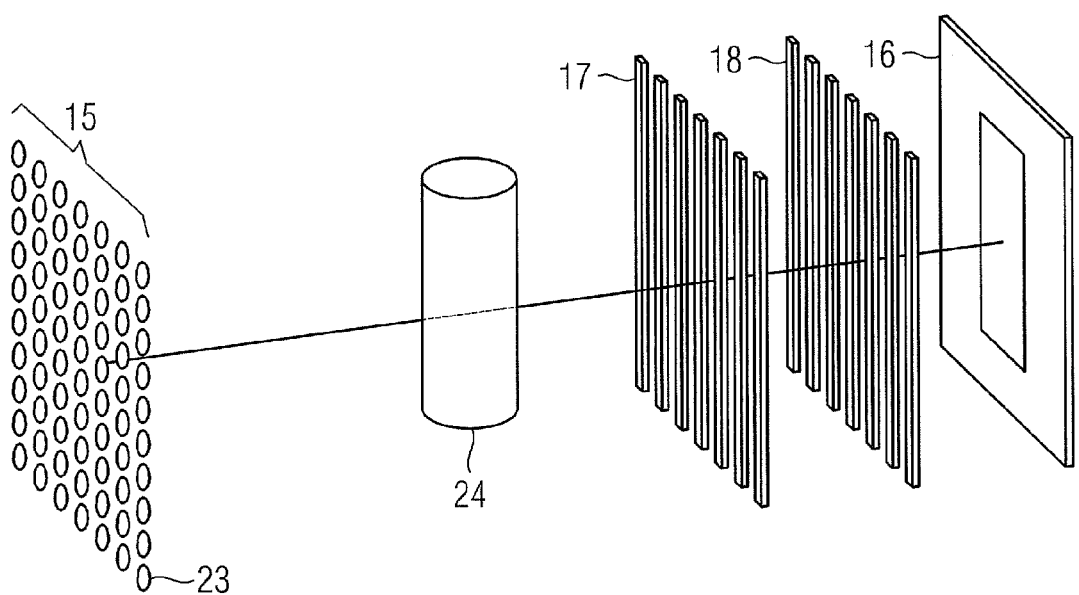
FIG. 3 shows a typical layout of a recording unit for phase-contrast X-ray imaging with a field-emission tube assembly.

Phase-contrast X-ray imaging exploits the fact that different types of body tissue diffract X-ray beams to different degrees. The basic layout employed in phase-contrast X-ray imaging by means of field-emission X-ray sources 23 generating coherent radiation is shown in FIG. 3. The coherent X-ray radiation penetrates an examination subject 24. By means of the gratings the coherent radiation is deflected in a known manner, an interference pattern is generated and converted accordingly into intensity fluctuations. The measured signal profile then contains quantitative information concerning the phase gradient of the examination subject. In this case the amplitude grating 18 is advantageously moved vertically with respect to the radiation direction of the X-ray radiation, for example by means of a motor or a piezoelectric actuator.

Figure 6:
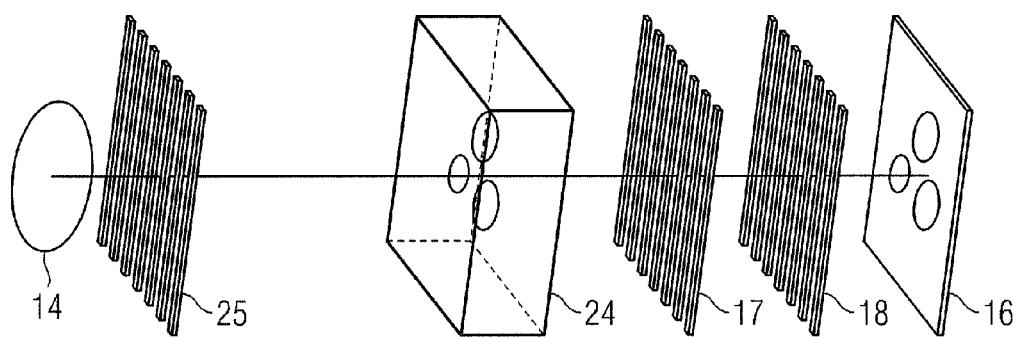
FIG. 6 shows a layout of an X-ray imaging system for phase-contrast X-ray imaging according to the prior art.
Figure 7:
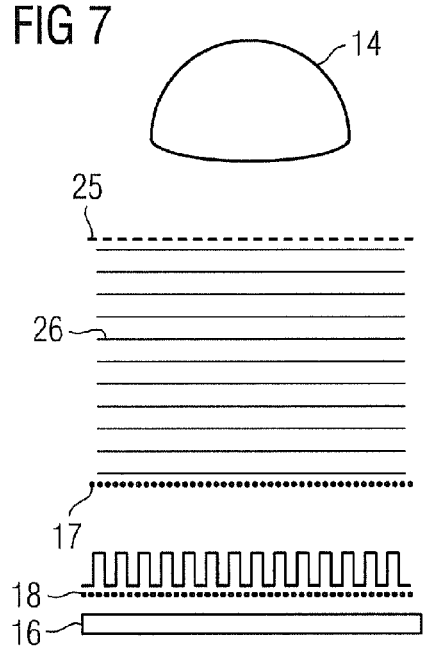
FIG. 7 shows a diagram of the radiation profile and the phase gradient during phase-contrast X-ray imaging without examination subject according to the prior art.
Figure 8:
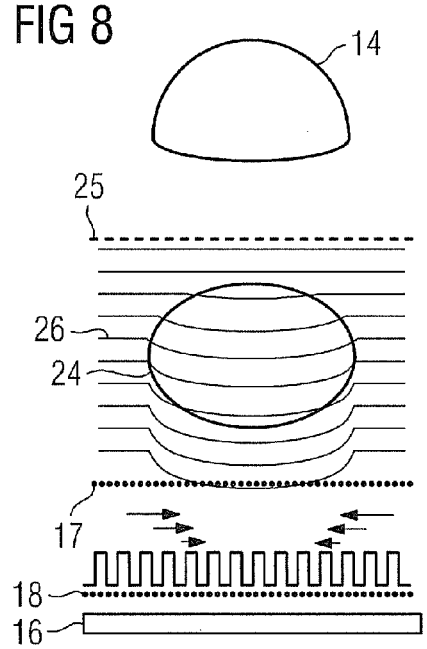
FIG. 8 shows a diagram of the radiation profile and the phase gradient during phase-contrast X-ray imaging with examination subject according to the prior art.
Figure 8:
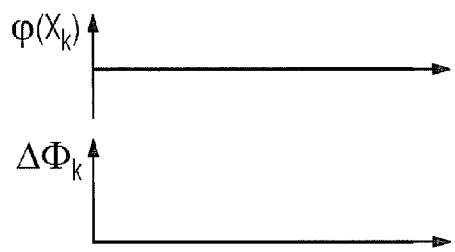
Figure 8:
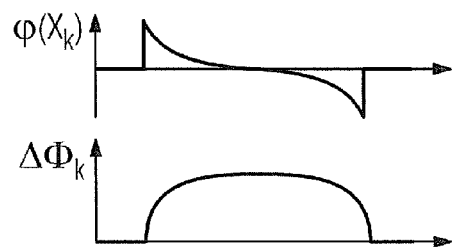

FIG. 6 shows a typical arrangement used in phase-contrast X-ray imaging, having three gratings coordinated with one another, having a coherence grating 25 for generating coherent radiation from a non-coherent, conventional X-ray tube assembly 14, having the phase grating 17 for generating interference lines, and having the amplitude grating 18 for reading out the generated interference pattern. The known radiation profile without and with examination subject is shown in FIGS. 7 and 8 respectively. Coherent radiation 26 generated by means of the conventional X-ray tube assembly 14 and the coherence grating 25 is incident on the phase grating 17, causing an interference pattern to be generated. The amplitude grating 18 disposed in front of the X-ray detector 16 is used for reading out the interference pattern. The amplitude grating 18 is moved and converts local interference lines into intensity fluctuations. The measured signal profile contains quantitative information concerning the phase gradient $\phi$ of the examination subject 24.

The recording units 10 and 11 or, as the case may be, the two C-arms 12, 13 (FIG. 1 and FIG. 2) can for example be arranged offset relative to each other in such a way that the C-arm planes spanned by the C-arms are offset by approx. 90° relative to each other; other angles can also be used, however. In this context a C-arm plane is understood to mean the plane which penetrates the C-arm essentially centrally along its circumference and divides the C-arm into two halves.

The two recording units 10 and 11 are jointly disposed on a retaining fixture so as to be adjustable or pivotable, by means of a pivot joint 19 for example. The retaining fixture can be formed for example by a ceiling stand 21 which can be moved along the ceiling—as shown in FIG. 1—or by a robotic arm 22 such as the 6-axis articulated-arm robot—as shown in FIG. 2. The retaining fixtures can be secured to the floor, to a ceiling, to a wall or to a patient positioning device 20. Motorized drive units (electric, hydraulic or pneumatic) can be used in order to assist the movements of the recording units. With the aid of the biplane X-ray imaging systems it is possible to acquire X-ray images in rapid succession by means of the two recording units. Thus, for example, the second recording unit is positioned in such a way that an overview X-ray image of an examination subject can be recorded; the X-ray image is recorded and the biplane X-ray imaging system is then pivoted so that a detailed image of a sub-region of the examination subject can be recorded by means of the first recording unit.

Alternatively to the C-arm the first and/or second recording unit can have the shape of a U-arm, or X-ray tube assembly and X-ray detector can each be disposed individually on retaining elements such as robotic arms, such that up to four retaining elements may be present.

The biplane X-ray imaging system additionally has a patient positioning device 20 for positioning an examination subject (patient or part of the body, such as a hand, arm, leg of the patient). The patient positioning device can be adjusted either manually or in a motor-driven manner in its height and in the longitudinal and/or transverse direction. The patient positioning device can be floor-mounted, wall- or ceiling-mounted and optionally inclined in the x-y-z direction as well as rotated about a central point. The patient positioning device can also perform circular or elliptical rotary movements about a fixed point in the plane or in space.

The biplane X-ray imaging system can also be used for 3D or 4D imaging.

The invention can be briefly summarized as follows: For particularly good applicability there is provided a biplane X-ray imaging system having two recording units disposed in different planes, each such unit having an X-ray detector and an X-ray source, wherein the first recording unit is formed by a phase-contrast recording unit for phase-contrast X-ray imaging. A second recording unit has a conventional arrangement. Such a biplane X-ray imaging system has the advantage of more effectively adapting medical imaging in respect of minimally invasive interventions or operations, since it is possible both to achieve fast X-ray images of a larger organ region in acceptable resolutions and in addition to acquire images of a smaller section at maximum resolution and with maximum quality.

The invention claimed is:

1. A biplane X-ray imaging system, comprising:
a first recording unit disposed in a first plane having a first X-ray detector and a first X-ray source that is a phase-contrast recording unit for phase-contrast X-ray imaging; and
a second recording unit disposed in a second plane having a second X-ray detector and a second X-ray source that is a conventional recording unit for conventional X-ray imaging,
wherein the first X-ray source is an X-ray tube assembly comprising a plurality of field-emission X-ray sources, and
wherein the plurality of field-emission X-ray sources are arranged in a two-dimensional matrix-type arrangement.

2. The biplane X-ray imaging system as claimed in claim 1, wherein the plurality of field-emission X-ray sources transmit quasi-coherent X-ray radiation.

3. The biplane X-ray imaging system as claimed in claim 2, wherein each of the field-emission X-ray sources comprises field-emission cathodes having a nanostructured material and carbon nano tubes.

4. The biplane X-ray imaging system as claimed in claim 1, wherein the first recording unit further comprises a grating disposed behind the first X-ray source for generating coherent X-ray radiation.

5. The biplane X-ray imaging system as claimed in claim 1, wherein the first recording unit further comprises:
- a phase grating disposed between an examination subject and the X-ray detector, and
- an amplitude grating disposed between the phase grating and the X-ray detector.

6. The biplane X-ray imaging system as claimed in claim 5, wherein the first recording unit comprises a device for moving the amplitude grating vertically with respect to a radiation direction of an X-ray radiation emitted by the first X-ray source.

7. The biplane X-ray imaging system as claimed in claim 1, wherein the first recording unit comprises a solid-state-based flat-panel detector and a C-arm.

8. The biplane X-ray imaging system as claimed in claim 1, wherein the second recording unit comprises a solid-state-based flat-panel detector and a C-arm.

9. The biplane X-ray imaging system as claimed in claim 1, wherein the first and the second recording units are disposed on a robotic arm.

10. The biplane X-ray imaging system as claimed in claim 9, wherein the robotic arm is a 6-axis articulated-arm robot.

11. The biplane X-ray imaging system as claimed in claim 1, wherein the field-emission X-ray sources are homogeneous and are uniformly arranged for transmitting coherent X-ray radiation upon being activated.

\* \* \* \* \*